United States Patent [19]
Kwun et al.

[11] Patent Number: 5,457,994
[45] Date of Patent: Oct. 17, 1995

[54] NONDESTRUCTIVE EVALUATION OF NON-FERROMAGNETIC MATERIALS USING MAGNETOSTRICTIVELY INDUCED ACOUSTIC/ULTRASONIC WAVES AND MAGNETOSTRICTIVELY DETECTED ACOUSTIC EMISSIONS

[75] Inventors: Hegeon Kwun; Cecil M. Teller, II, both of San Antonio, Tex.

[73] Assignee: Southwest Research Institute, San Antonio, Tex.

[21] Appl. No.: 33,256

[22] Filed: Mar. 16, 1993

Related U.S. Application Data

[63] Continuation-in-part of Ser. No. 973,152, Nov. 6, 1992.
[51] Int. Cl.⁶ .......................... G01N 29/14; G01N 29/28
[52] U.S. Cl. ................................. 73/587; 73/594; 73/643
[58] Field of Search .......................... 73/587, 594, 643

[56] References Cited

U.S. PATENT DOCUMENTS

| | | | |
|---|---|---|---|
| 4,309,903 | 1/1982 | Ono | 73/587 |
| 4,352,038 | 9/1982 | Moreton | 73/587 |
| 4,593,565 | 6/1986 | Chamuel | 73/643 |

FOREIGN PATENT DOCUMENTS

| | | | |
|---|---|---|---|
| 0083654 | 4/1987 | Japan | 73/594 |
| 1507940 | 9/1989 | U.S.S.R. | 73/594 |

Primary Examiner—Hezron E. Williams
Assistant Examiner—Rose M. Finley
Attorney, Agent, or Firm—Gunn, Lee & Miller

[57] ABSTRACT

A method and apparatus for the nondestructive evaluation of ferromagnetic and non-ferromagnetic materials, particularly wire ropes, cables, and strands, and pipes utilizing the magnetostrictive effect for measuring minute variations in magnetic fields and characterizing these minute variations as indicative of the acoustic/ultrasonic behavior of fractures, cracks, and other anomalies within a substance under evaluation. The apparatus and method contemplate both an active testing application, wherein a transmitting sensor generates an acoustic/ultrasonic pulse within a material through the magnetostrictive effect and a second receiving sensor detects reflected acoustic/ultrasonic waves within the material, again by the inverse magnetostrictive effect. The advantages of utilizing magnetostrictive sensors as opposed to well known piezoelectric sensors lies in the ability to generate and detect acoustic/ultrasonic waves without a direct physical or acoustical contact to the material. The apparatus and method of the present invention also anticipates the use of a passive monitoring system comprised only of a receiving magnetostrictive sensor that continuously monitors a ferromagnetic or non-ferromagnetic substance for acoustic emissions and either records this monitored information or alerts the appropriate personnel of the existence of an acoustic emission indicating deterioration within the structure.

5 Claims, 11 Drawing Sheets

NONDESTRUCTIVE EVALUATION OF NON-FERROMAGNETIC MATERIALS USING MAGNETOSTRICTIVELY INDUCED ACOUSTIC/ULTRASONIC WAVES AND MAGNETOSTRICTIVELY DETECTED ACOUSTIC EMISSIONS

This application is a Continuation in Part of application Ser. No. 07/973,152, filed Nov. 6, 1992, pending.

BACKGROUND OF THE INVENTION

1. Field of the Invention

The present invention relates generally to nondestructive testing (NDT) of ferromagnetic ropes, cables, strands and prestressed tendons (in concrete) for flaws and fractures. The present invention relates more specifically to the nondestructive evaluation of ferromagnetic ropes, cables, strands, and prestressed tendons for flaws and fractures using magnetostrictively induced acoustic/ultrasonic waves, and the passive monitoring of crack growth and fractures through the magnetostrictive detection of acoustic emissions (AE). The present invention, in particular the detection of AE, also applies to NDT of other materials such as pipes, tubes, and plates.

2. Description of the Prior Art

The deterioration (corrosion and fracture) of individual wires which make up the main cables of structures such as suspension bridges, and the stays of cable stayed bridges, is a serious problem. Many of these bridges in the United States are well over 50 years old and the importance of addressing this problem has only increased in recent years. In order to repair and maintain these cables for bridge safety, a means for the nondestructive evaluation (NDE) of these cables for fractured wires and corrosion is urgently needed.

There currently are a number of NDE methods known in the art, whereby ultrasonic waves are used to detect the presence of breaks, fractures, corrosion, and the general deterioration of strands within a cable. Unfortunately, the ultrasonic methods described to date require some means for direct physical/acoustic contact to introduce the ultrasonic waves into the individual wires under study. Except for a few cases where the end of a cable is exposed and individual wires of the cable have sufficient exposure for transducer coupling, introducing ultrasonic waves into the individual wires in this manner is generally impractical.

The terminations, socketed areas, regions under the cable bands, and regions over the tower saddles are all generally inaccessible for existing NDE techniques such as DC magnetic field leakage and transverse impulse vibrational wave methods. These areas of cable are typically in direct contact with other structural members and, as such, cannot be readily analyzed using techniques that involve field leakage from the cable or vibrational analysis of the cable.

The stress forces associated with an ultrasonic wave traveling within a cable or metal strand change the magnetic induction of the ferromagnetic material due to the magnetostrictive effect. These changes in the magnetic induction within the cable or strand can be detected using a pick-up coil placed around or on the cable or strand.

U.S. Patent No. 3,115,774, issued to Kolb, describes a magnetostrictive drill string logging device that incorporates a vibration sensor and takes advantage of the magnetostrictive properties of the metallic drill string. Unfortunately, the accuracy of the vibration sensor utilized in the Kolb patent greatly limits the ability of the patented device to help analyze or "log" the condition of the drill string within a drill hole. While the Kolb patent discloses the use of the magnetostrictive principle to generally analyze conditions along a ferromagnetic strand, it does not disclose an apparatus and method of sufficient refinement to allow a specific analysis of the corrosion, deterioration, or fractures that might be found in something such as a ferromagnetic steel cable.

An article published in 1982 in the book "Ultrasonic Testing" edited by J. Szilard, describes the application of magnetostrictive techniques to wire rope testing for fractured strands and corrosion. However, no description of an apparatus or a method for implementation of the concept is provided in this disclosure and, in general, the article simply describes or predicts the ability to use the physical magnetostrictive principle to detect defects in wire ropes or bridge cables. The Szilard article does disclose the use of a spiraling wave that is generated magnetostrictively to detect cracks within a single rod. Such spiraling waves, however, have a very limited range over which their analysis is practical. The technique described, therefore, does not lend itself to applications using long ropes or cables.

U.S. Pat. No. 4,979,125, issued to one of the inventors of the present application, describes a nondestructive means for evaluating wire ropes and cables by using the transverse impulse vibrational wave method. This method permits the detection of flaws by recognizing certain vibrational wave amplitude and distribution patterns resulting from striking the test cable or strand with a transverse force. Tension on a test strand or cable is calculated by measuring the propagation velocity of the vibrational waves through the test object. The distribution in both amplitude and time of the waves that result allows an analysis of the existence of flaws and variations in the tension across a length of rope that may not be accessible. This transverse vibrational wave method of analysis, however, is not appropriate for many areas where the vibration of the rope is effected by external components of the bridge structure or other external forces on the free movement of the wire strands.

It would, therefore, be advantageous to develop an NDE method useful for testing ferromagnetic wires, ropes, and wire strands and the like which would not require a direct access to the material under test. It would be advantageous if such a remote system could detect minor, as well as major rope flaws, stresses, and corrosions.

One method for monitoring the fracturing of wires in a steel cable or strand is by acoustic emission (AE) detection using a piezoelectric sensor. This requires a precise acousting coupling with the strand through direct physical contact between the sensor and the strand. It also typically involves a certain amount of surface preparation such as the removal of paint and corrosion in the immediate area. The durability of such sensors, when maintained in direct contact with the cable strands, very low. It is also quite complicated to install such piezoelectric sensors and careful analysis of the area of coupling is required to eliminated the effects of immediate structural discrepancies. The systems are also typically quite expensive, not only in apparatus costs, but in installation costs as well.

It is also known to use ultrasonic detectors to passively monitor acousting emissions generated by progressing fractures within a cable or metallic strand. Typically, such applications utilize piezoelectric sensors that must be physically and acoustically coupled to the material under analysis. It is also apparent that frequency sensitivity limits the range and accuracy of such methods, even if the coupling requirements are met.

a. Background on the Magnetostrictive Effect

The magnetostrictive effect is a property that is peculiar to ferromagnetic materials. The magnetostrictive effect refers to the phenomena of physical dimensional change with variations in magnetization. The effect is widely used to make vibrating elements for sonar transducers, hydrophones, and magnetostrictive delay lines for electric signals. It has also been used to excite spiraling waves in a steel rod or wire of diameters up to 14 mm for nondestructive inspection during the process of drawings the steel rod. This approach for using the magnetostrictive effect with steel rods upon drawing is similar to the non-contact generation and detection of ultrasonic waves in non-ferrous materials using electromagnetic acoustic transducers that rely on the Lorentz force.

In magnetostrictive delay line applications, the generation and detection of ultrasonic waves is typically achieved by the introduction of a sinusoidal or pulsed current into a transmitting coil surrounding a magnetostrictive delay line which is typically no more than 1 in diameter. The change of magnetization within the rod or line located within the transmitting coil causes the material to change its length locally in a direction parallel to the applied field. This abrupt local dimensional change, which is the magnetostrictive effect, generates a stress wave that simultaneously travels at the speed of sound within the material towards both ends of the rod. When the stress wave is reflected back from the end of the rod, or from a defect in the rod and reaches a receiving coil, which is in many respects similar to the transmitting coil, it generates a changing magnetic flux in the receiving coil as a result of the inverse magnetostrictive effect. This changing magnetic flux in turn induces an electric voltage within the receiving coil that is proportional to the magnitude of the stress wave. The magnetostrictive effect is independent of the direction of the applied magnetic field, so an equivalent stress is generated during each half cycle of the applied magnetic field and the frequency of the stress wave is twice that of the current applied to the transmitting coil. The frequency of the stress wave can be made the same as that of the current by applying a bias magnetic field to the rod using a permanent magnet or an electromagnet.

b. Comparison of Rope/Cable NDE Methods

The present invention utilizes the ability of the magnetostrictive effect to induce and detect acoustic/ultrasonic waves in ferromagnetic material without direct physical contact with the material. This approach overcomes the difficulties in applying conventional ultrasonic techniques to NDE of bridge cables and strands. Table 1 provides a summary comparison of techniques, including the present inventions magnetostrictive acoustics/ultrasonics approach, as applied to wire ropes and cables. The present invention also provides a number of advantages over conventional methods when applied to AE monitoring as summarized in Table 2.

TABLE 1

COMPARISON OF ROPE/CABLE NDE METHODS

|  | Magnetic Flux Leakage | Transverse Impulse Vibrational Wave | Magnetostrictive Acoustics/ Ultrasonics (MsAU) |
| --- | --- | --- | --- |
| Principle | Detection of magnetic leakage field caused by wire breaks | Detection of mechanical vibrational signals reflected | Detection of acoustic/ultra sonic signals reflected from defects |
| Applicable Material | Ferromagnetic | from defects Metals, nonmetals | Ferromagnetic, extendable to non-ferromagnetic |
| Sensors | Electro- or permanent magnet, magnetic-field sensor (e.g., Hall probe) | Mechanical impulse generator (e.g., hammer), displacement sensor | MsAU transmitter and receiver |
| Couplant | Not required | Not required | Not required |
| Inspection Range | About the size of sensor | Hundreds of feet or more | Hundreds of feet or more |
| Scanning | Required | Not required | Not required |
| Detectable Defect Size | Variable | 10% or higher cross-sectional area change | 4% or less cross-sectional area change |
| Inspection of Obstructed Areas (such as sockets, saddles, bands) | No | No | Yes |
| Portability of Equipment | Poor | Good | Good |
| Simplicity of Data Documentation and Analysis | Moderate | Moderate to high | High |

TABLE 2

COMPARISON OF MAGNETOSTRICTIVE ACOUSTIC EMISSION (MsAE) AND CONVENTIONAL ACOUSTIC EMISSION (AE) METHODS

|  | MsAE | Conventional AE |
| --- | --- | --- |
| Sensor | Magnetostrictive | Piezoelectric |
| Couplant | Not required | Required |
| Physical Contact to the Part | Not required | Required |
| Surface Preparation (removal of paint, etc.) | Not required | Required |
| Sensor Durability (under physical abuse and weather) | High | Low |
| Sensor Installation | Simple | Complicated |
| Cost | Low | High |

SUMMARY OF THE INVENTION

It is therefore an object of the present invention to provide an apparatus and method for the nondestructive evaluation of ferromagnetic ropes, cables, or strands that detects flaws, fractured wires, and corrosion therein.

It is another object of the present invention to provide an apparatus and method for the nondestructive evaluation of ferromagnetic cables, ropes, or strands that utilizes the magnetostrictive effect to indicate the presence of flaws, fractures, or corrosive effects within the cable, rope, or strand, including areas that are not normally accessible to direct ultrasonic analysis.

It is another object of the present invention to provide an apparatus and method for the passive AE monitoring of ferromagnetic cables, ropes, strands, and other structures such as pipes, tubes, and plates that utilizes the magnetostrictive effect to detect acoustic emissions from progressing flaws, fractures, or corrosive effects.

It is another object of the present invention to provide an apparatus and method for the non-destructive evaluation of non-ferromagnetic ropes, cables or strands that detects flaws, fractured strands and deterioration therein.

It is another object of the present invention to provide an apparatus and method for the non-destructive evaluation of non-ferromagnetic cables, ropes or strands that utilizes the magnetostrictive effect within ferromagnetic materials placed in mechanical contact with the non-ferromagnetic structures, to indicate the presence of flaws, fractures or corrosive effects within the cable, rope or strand, including areas that are not normally accessible to direct ultrasonic analysis.

It is finally an object of the present invention to provide an apparatus and method for the passive AE monitoring of non-ferromagnetic cables, ropes, strands and other structures such as composite components, pipes, tubes and plates that utilizes the magnetostrictive effect within ferromagnetic materials mechanically attached to the non-ferromagnetic material to detect acoustic emissions from progressing flaws, fractures or other corrosive effects.

Accordingly, the present invention provides an apparatus and method that utilize the magnetostrictive effect to generate and detect acoustic/ultrasonic waves in a ferromagnetic cable. One application of the present invention involves encircling a cable under inspection with a coil of a predetermined number of turns and energizing the coil with a pulse or tone-burst electric current so as to induce and transmit an acoustic/ultrasonic wave (by way of the magnetostrictive effect) in individual wires comprising the cable. This acoustic/ultrasonic wave results from a change of magnetization within the cable located within the transmitting coil. This change in magnetization causes the individual wire to change its length locally. This abrupt local dimensional change as a result of the magnetostrictive effect generates a stress wave of acoustic/ultrasonic frequency that simultaneously travels along the cable in both directions. When this acoustic/ultrasonic wave is reflected back from the ends of the cables or from areas in the cable with fractures, or other anomalies that might reflect the wave, it is returned to a receiving coil where it in turn generates a changing magnetic flux as a result of the inverse magnetostrictive effect. This changing magnetic flux can be detected by an appropriate coil sensor.

The detection of the reflected acoustic/ultrasonic waves from discontinuities in the cable using a sensing coil can be made either globally using an encircling coil, or locally using an array of separate local sensors. The process of the present invention then amplifies, processes, displays, and analyzes the detected signal. Sufficient experimental use with known anomalies and flaws in a cable can establish an appropriate data base and background of information to identify the characteristics of anomalies, fractures, corrosion, etc., seen within the cable.

The apparatus and method of the present invention can be applied in a passive mode to monitor acoustic emissions from the progressive growth of flaws in cables, pipes, or plates. Such an application would serve as a long term monitoring means capable of recording information on detected emissions or transmitting an alarm on the occurrence of an emission exceeding a specified level.

The apparatus and method of the present invention can, in addition to being applied to bridge cables, be applied to the inspection of other steel cables and ropes, including, but not limited to drag lines, ski lifts, mining cables, elevator cables, and crane wire ropes and ferromagnetic pipings and tubings.

The geometry of the structures to which the apparatus and method of the present invention can be applied is generally not limiting, but the present invention lends itself most effectively to the NDE of elongated structural elements. This allows for better isolation of the location of an anomaly in what can be roughly characterized as a linear body.

Apart from solid cables and the like, the most common application of the present invention to flaw detection is with elongated ferromagnetic pipe and tubing. The acoustic emission monitoring capabilities of the present invention are, however, applicable to any type of structure.

DETAILED DESCRIPTION OF THE PREFERRED EMBODIMENTS

Figure 1:
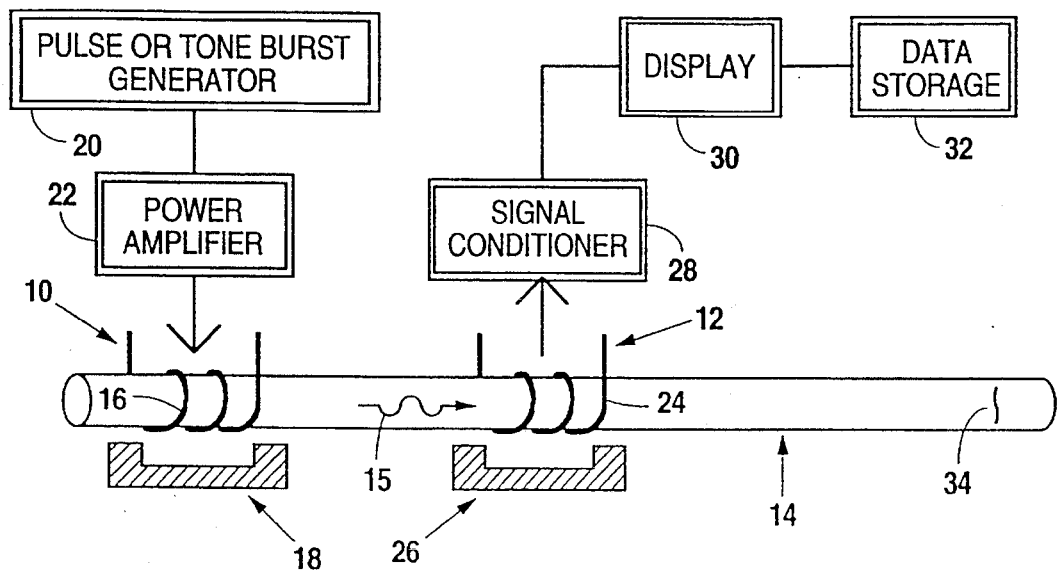
FIG. 1 is a schematic representation of the test apparatus of the present invention appropriate for the active magnetostrictive generation and detection of acoustic/ultrasonic waves within a ferromagnetic rope or cable under test.

Reference is first made to FIG. 1 for a detailed description of the arrangement of the testing apparatus necessary for the implementation of the method of the present invention, providing for the generation and detection of acoustic/ultrasonic waves. In this active testing embodiment of the present invention, both transmitting assembly (10) and receiving assembly (12) are required. The specific structures of transmitting and receiving assemblies (10 and 12) are discussed in more detail below with respect to FIGS. 3 and 4.

While no direct acoustic coupling to material (14) under examination is required, the apparatus must be placed and arranged proximate to the ferromagnetic steel cable, wire rope, or ferromagnetic pipe, etc., that the evaluation is being carried out on. The sensors can be operated at a distance of more than several centimeters from the ferromagnetic material. Transmitting assembly (10) that is positioned close to material (14) under evaluation is comprised primarily of transmitting coil (16) and bias magnet (18). A pulse or tone-burst generator (20) is coupled through power amplifier (22) to transmitting coil (16) and generates a signal appropriate to effect an acoustic/ultrasonic wave (15) within material (14) under evaluation.

Receiving assembly (12) of the apparatus of the present invention is configured much like transmitting assembly (10) and is comprised primarily of receiving coil (24), also encompassing or positioned adjacent to material (14) under evaluation, as well as bias magnet (26). The signals received by receiving coil (24) are conditioned by signal conditioner (28) and may be displayed directly on display (30) or stored for later review and analysis in data storage device (32). Bias magnets (18 and 26) may not need to be present in every instance, if a sufficient residual magnetization is left in the material under study.

The method of the present invention, as applied to the combined generation and detection of acoustic/ultrasonic waves within a material, is generally carried out on a test by test basis. That is, it is not typical to simply install transmitting and receiving assemblies (10 and 12) and leave them in place, as with an alternative embodiment of the present invention described later, but only to temporarily install assemblies (10 and 12) in proximity to material (14) under test for the purpose of carrying out the analysis.

One benefit of the present invention is that installing assemblies (10 and 12) requires no physical, electrical, or acoustic coupling to material (14) under evaluation. Transmitting assembly (10) and receiving assembly (12) may be proximate to each other as is shown in FIG. 1 or they may be apart from each other as long as their spacial relationship is known. It is also possible that transmitting coil (16) and receiving coil (24) could be incorporated in a single transducer if appropriate consideration is given for the resultant inductive effects.

Use of the magnetostrictive effect involves creating a variation in the magnetic field in and around material (14) under evaluation. Pulse or tone-burst generator (20), by way of power amplifier (22), supplies a voltage to transmitting coil (16) that abruptly changes the magnetic field created by bias magnet (18) in proximity to material (14). This abrupt change in the magnetic field induces, because of the magnetostrictive effect, acoustic/ultrasonic wave (15) within material (14) that emanates from the area adjacent transmitting coil (16). The generated acoustic/ultrasonic wave (15) travels along material (14) in both directions (in FIG. 1, only the wave traveling to the right is shown). Wave (15), as indicated in FIG. 1, travels down the material and may initially pass through receiving coil (24) as shown. As with other methods wherein acoustic/ultrasonic waves are used for the nondestructive evaluation of materials, fractures, anomalies, etc., within the material will cause a reflection and/or modification of the wave. It is this reflected wave or modification of the incident wave that is detected. Receiving coil (24) is positioned so as to detect the modifications, reflections, etc., of acoustic/ultrasonic wave (15) as it travels through and is reflected back to receiving coil (24) from these anomalies.

For example, if fracture (34) existed in test material (14) where indicated, at a location apart from receiving coil (24), acoustic/ultrasonic wave (15) would travel through receiving coil (24) and pass fracture (34) to be partially reflected by fracture (34) back to receiving coil (24). If test material (14) is a steel cable consisting of a bundle of wires and some wires are fractured, the wave will be reflected from these fractured wires. This signal would be detected and identified as an anomaly according to patterns already established for the particular material under evaluation. The details of establishing these patterns and of detecting anomalies as a result of detected signals is described in more detail below with respect to FIG. 4.

Acoustic/ultrasonic wave (15) passing through material (14) proximate to receiving coil (24) creates a dilation/contraction in the ferromagnetic material which in turn alters the magnetic field within and about material (14). Bias magnet (26) establishes a baseline magnetic field that fluctuates as a result of the magnetostrictive effect caused by the passage of an acoustic/ultrasonic wave therethrough. A current/voltage is induced in receiving coil (24) as a result of this fluctuating magnetic field according to well known principles. This current or voltage created in receiving coil (24) is conditioned by signal conditioner (28) in such a way as to amplify and filter the signal to a level and range of frequencies appropriate for detecting anomalies. This conditioned signal is then displayed on an oscilloscope or other such amplitude versus time display (30) and may be recorded in data storage device (32) for later display and analysis in time domain, or frequency domain. Again, the specifics of analyzing the signal received by the method described herein are discussed in more detail below.

Figure 2:
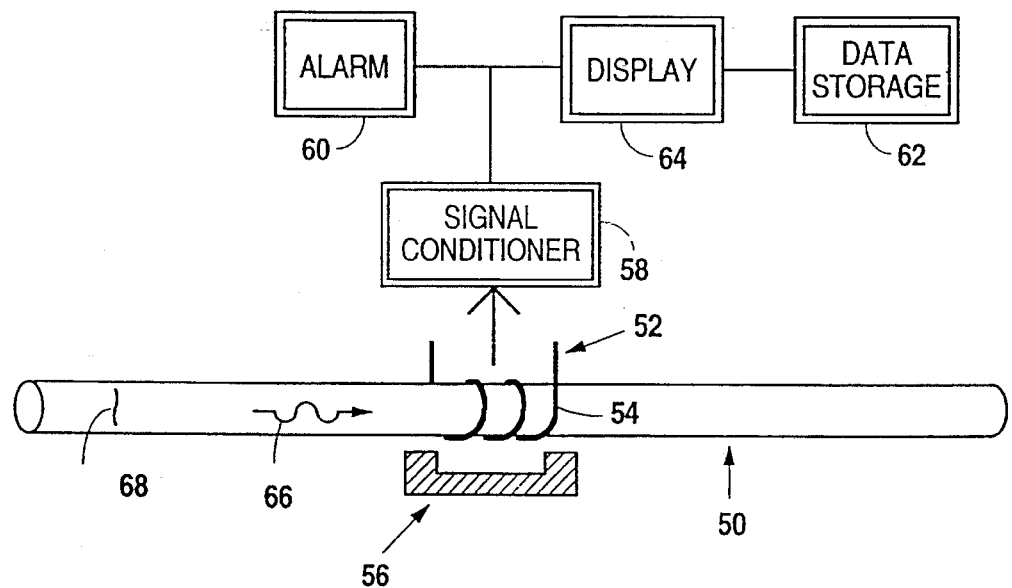
FIG. 2 is a schematic representation of the test apparatus of the present invention appropriate for the passive magnetostrictive monitoring of acoustic emissions within a ferromagnetic rope or cable under test.

Reference is now made to FIG. 2 for a detailed description of an apparatus appropriate for implementation of the passive magnetostrictive AE monitoring embodiment of the present invention. The apparatus disclosed for this particular application of the present invention is quite similar to that disclosed in FIG. 1 with the exception of transmitting coil (16), bias magnet (18), and the associated electronics that would normally generate an acoustic/ultrasonic wave within material (50) under evaluation. Instead, the apparatus is comprised more simply of receiving assembly (52), made up of receiving coil (54), and bias magnet (56), connected to signal conditioner (58) and alarm apparatus (60) or data storage device (62). In addition, the arrangement contemplates an occasional hook up of display device (64) to the passive monitoring system.

The principle behind the application of the present invention disclosed in FIG. 2 is very similar to that of the application disclosed in FIG. 1 with the exception that the acoustic/ultrasonic acoustic wave (66) being detected by receiving coil (54) is generated not by a transmitting coil, but by fracture or crack growth (68) within sample material (50) itself. The whole purpose of this embodiment is to permanently install the apparatus on material (50) and thereby monitor crack growth and fracture of material (50) over a long period of time.

Clearly, it is not expected that an intermittent evaluation of material (50) will result in the detection of acoustic emissions from fractures, cracks, etc., within the material, but over a period of time, with continuous monitoring of the material it is anticipated that the AE from these occurrences can be detected and either recorded or alarmed in a manner described in more detail below.

As an example, if some individual wires of a steel cable (50) are fractured at a location (68) apart from receiving coil (54), as shown in FIG. 2, acoustic/ultrasonic waves (66) will be emitted and would propagate along the wires in both directions. These acoustic/ultrasonic waves (66) travel down material (50) in much the same way as the acoustic/ultrasonic waves described with the previous embodiment. In this case, the mere occurrence of a signal received at receiving coil (54) might indicate the presence of a fracture that requires attention.

Clearly, material (50) could be subject to other factors in the environment that could create acoustic emissions within the material and such factors would have to be accounted for in the detection of acoustic emissions. Factors such as signal intensity and repetition of the signal as a result of its reflection from the endpoints of the material under evaluation would contribute to an analysis that would allow isolation of the location of the source of the acoustic emission and the elimination of external factors. The process of monitoring a material for AE would involve the progressive establishment of an acoustic emission "signature" for the material under unfractured conditions and thereafter a monitoring of changes to this acoustic emission signature.

The structure of the apparatus necessary for carrying out this long-term magnetostrictive monitoring of acoustic emissions is simple and inexpensive enough that such monitoring systems could be placed with relative frequency about a structure to be evaluated. Little more than the receiver assembly and a means for electronically recording the signal are required for implementation of this apparatus and method. It is anticipated, as will be discussed in more detail below, that for large structures there might be multiple receiving coils, all connected to a single data storage or recording device.

It is anticipated that the apparatus described as being used with solid cables or wires in FIGS. 1 and 2 could, as described earlier, be used with pipes or tubes. It is not essential that the sensor coils encompass the entire cross section of the material under study, as will be seen with respect to FIG. 3 below. The material under evaluation could be in the nature of a liquid or gas pipeline with major inaccessible areas underground. In such a case, the attachment of a coil sensor adjacent a terminal surface of the pipeline would be sufficient for sensing of an acoustic emission. Transmissions of an acoustic/ultrasonic wave can be made from the outside or the inside of the pipe.

Figure 3:
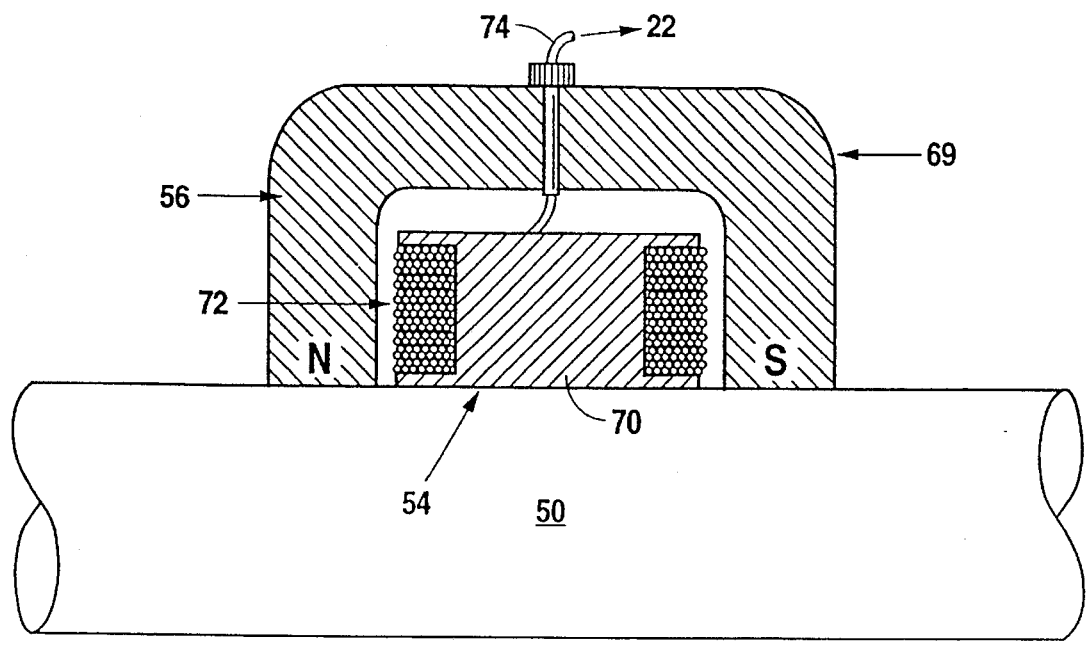
FIG. 3 is a detailed view of the magnetic coil and bias magnet assembly appropriate for locally detecting the magnetostrictive effect caused by acoustic/ultrasonic waves within a ferromagnetic rope or cable under test.

Reference is now made to FIG. 3 for a detailed description of the structure of a typical magnetostrictive AE sensor (69) as would be appropriate for attachment to a flat or curved ferromagnetic surface. FIG. 3 discloses both the positioning of permanent bias magnet (56) for establishing a base-line magnetic field within ferromagnetic material (50), and receiving coil (54) that are both placed in proximate position to ferromagnetic material (50). Coil (72), whose number of windings about bobbin (70) may be experimentally determined by the specific material under evaluation, is connected by means of electrical cable (74) to signal conditioner (28) described previously. In this particular embodiment, permanent bias magnet (56) that establishes the bias field within sample material (50) also serves to attach sensor (69) to material (50).

AE sensor (69) serves primarily as a receiving coil, although the same structural configuration of the sensor could be utilized as a transmitting coil as well. Once again, the permanent magnet would serve as a magnet for biasing of the field within the material and the electromagnetic coil would serve as a means for altering that magnetic field to induce, through the magnetostrictive effect, an acoustic/ultrasonic wave.

Figure 4:
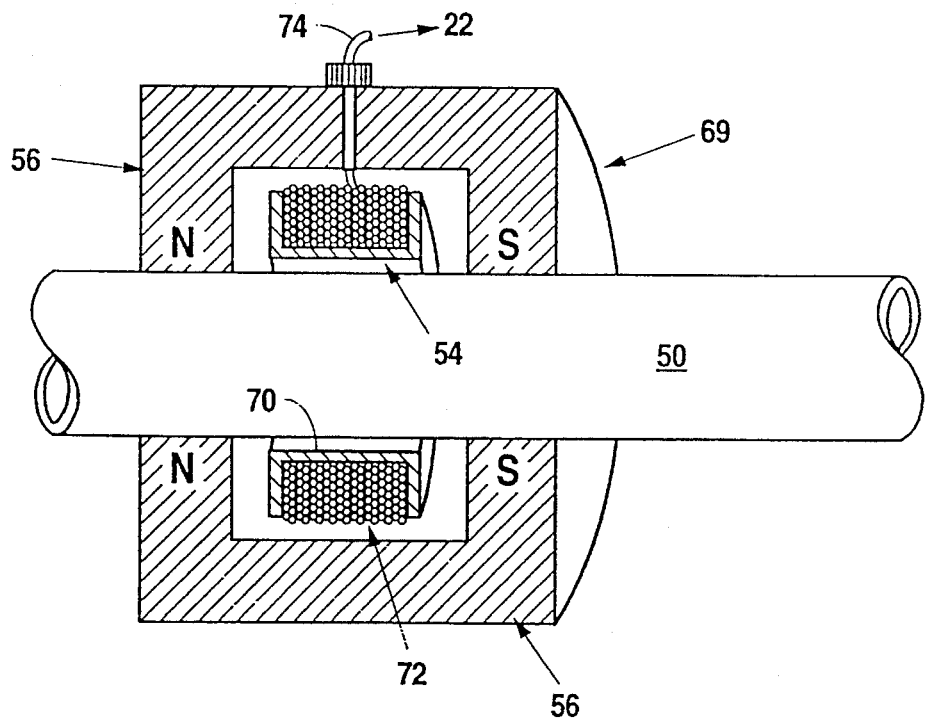
FIG. 4 is a detailed view of the magnetic coil and bias magnet assembly appropriate for transmitting and globally detecting the acoustic/ultrasonic waves in ferromagnetic cable stays, strands, and/or suspender ropes.

Reference is now made to FIG. 4 for a detailed description of the structural configuration of a transmitting and/or receiving transducer for implementation of either the magnetostrictive acoustic/ultrasonic embodiment of the present invention or the magnetostrictive AE monitoring embodiment of the present invention. In this case, sensor (69) is cylindrical in nature and designed to envelope cylindrical cable strand, rod, or rope (50). The functional structure of sensor (69) is essentially the same as that shown in FIG. 3 and is comprised of bias magnet (56) and coil (54). In this case, coil (54) is enclosed within cylindrical permanent bias magnet (56), and both surround material (50) to be evaluated.

In the preferred embodiment, the installation of sensor (69) for AE monitoring purposes would involve the placement of sensor (69) about the material to be evaluated prior to its installation. It is also conceived that sensors (69) might retrofit to existing structures and that the structural characteristic shown in FIG. 4 of sensor (69) enclosing material (50) could be modified slightly to allow this enclosure to be accomplished without disturbing material (50). The use of "clamp on" sensors of this type are well known in the art.

Figure 5:
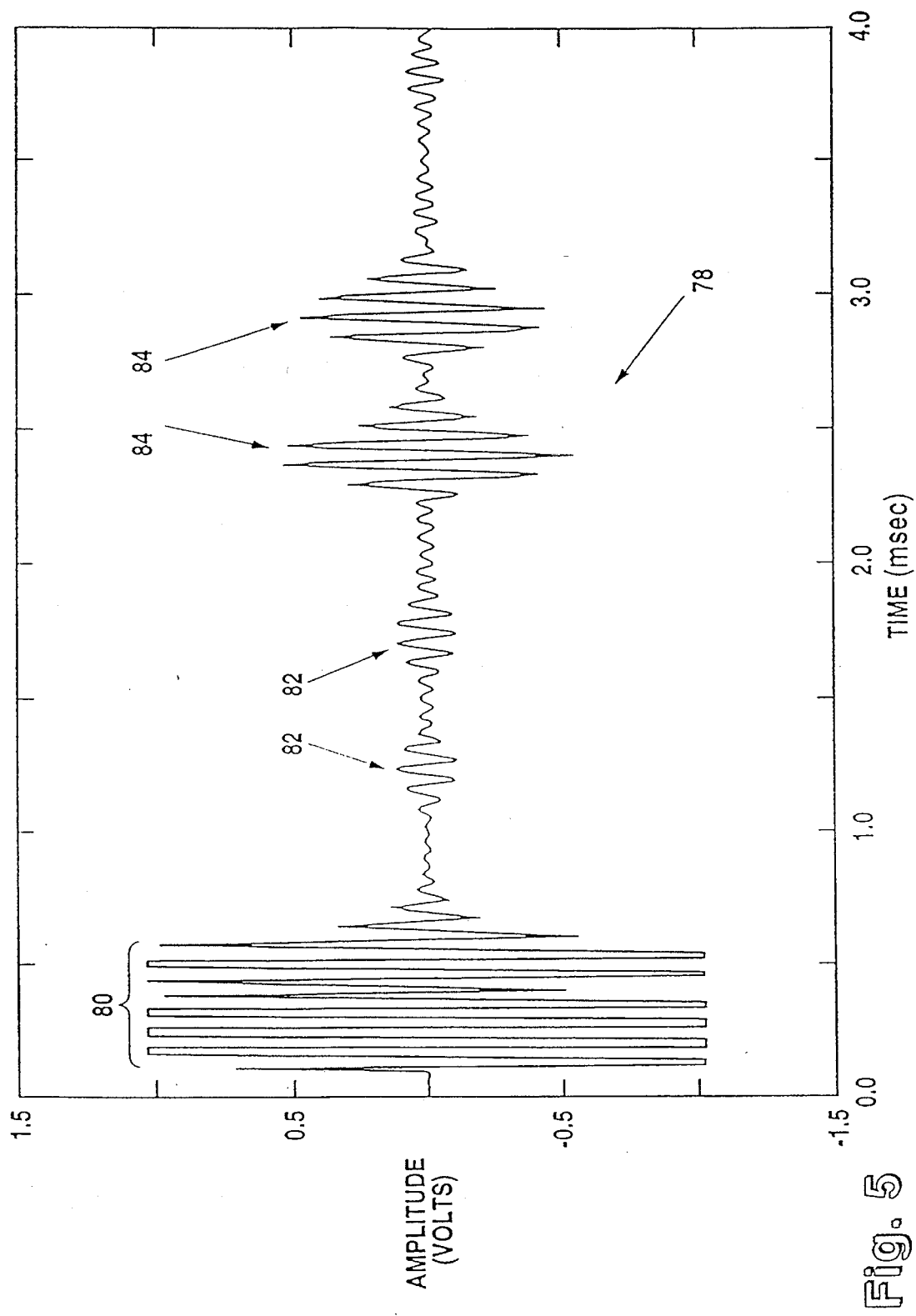
FIG. 5 is a graphic depiction of a output signal obtained using the apparatus of the present invention in the magnetostrictive generation and detection of acoustic/ultrasonic waves, showing the amplitude of the received signal over a period of time.

Reference is now made to FIG. 5 for a detailed description of a sample received signal (78) from the magnetostrictive acoustic/ultrasonic method of the present invention. The graphic representation shown in FIG. 5 displays received signal (78) as varying over time measured in milliseconds and amplitude measured in volts. The initial pulse (80) of signal (78) reflects the combination of the leakage signal coupled to the receiver through air when the transmitting coil is energized and the initial acoustic/ultrasonic pulse generated by the transmitting coil and received as the incident acoustic/ultrasonic wave passes through the receiving coil. Subsequent increases in amplitude (82) of the signal indicate reflected portions of the acoustic/ultrasonic wave that derive from anomalies, irregularities, or other fractures within the cable. Depending upon the placement of the receiving coil, defect signals (82) might be incident or reflected waves and can be isolated according to their time characteristics.

Finally, far-end reflected signals (84) are seen as generally larger than defect signals (82), but generally diminished below the amplitudes of initial pulse (80). The multiplicity of defect signals (82) and far end reflected signals (84) is the result of the finite length the sample material used to acquire the data and the double detection of the signals by the receiving coil before and after reflection from the near end of the sample.

To properly analyze the detector signals, it is necessary to accurately place and recognize the location of both the transmitting coil and the receiving coil in the implementation of the present method and apparatus. Once the geometry of the material under evaluation and the positioning of the apparatus for the system are well established, the time values involved in the received signal are utilized to determine the location of anomalies that contribute to the signal characteristics.

If the length of the material under study is short, it is possible to characterize a "signature" for a material to be evaluated, associated perhaps with its installation, and thereafter to reevaluate the material and obtain a new signature at some time after degradation and fractures might be expected to have occurred. A monthly or annual examination of a structure, for example, might produce a number of signal wave forms that can be compared one to the other, with their similarities characterized as initial pulses, end reflected signals, points of external contact, etc., and the distinctive areas between the signal signatures being indicative of changes in the integrity of the material.

Figure 6:
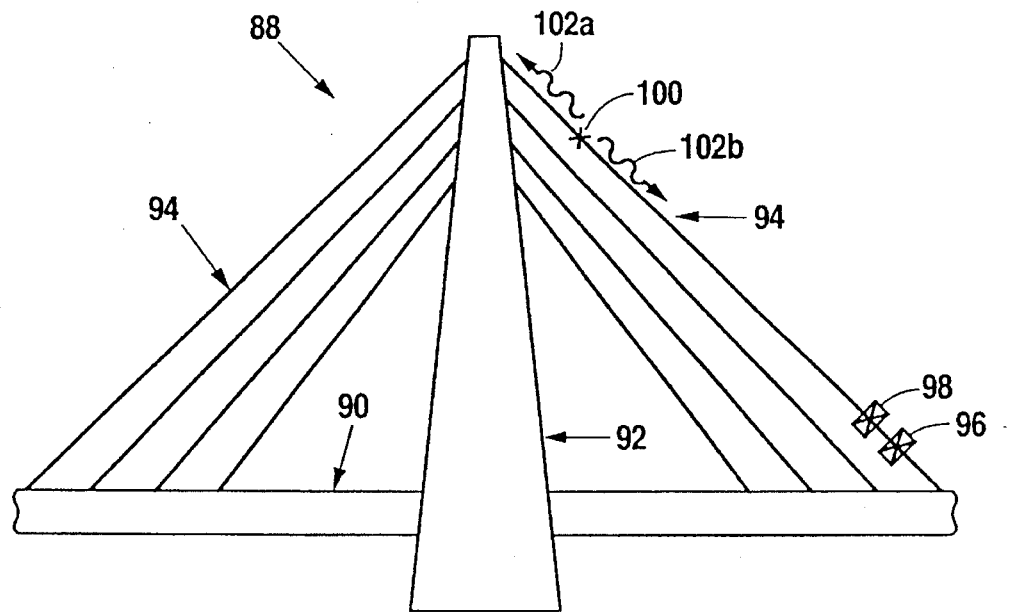
FIG. 6 is a schematic representation of the implementation of the apparatus of the present invention for the magnetostrictive acoustic/ultrasonic inspection of cable-stay bridge cables.

Reference is now made to FIG. 6 for a schematic representation of one method of installing a first embodiment of the present invention on cable-stay bridge cables. In this application of the active magnetostrictive acoustic/ultrasonic inspection method, receiving coil (98) and transmitting coil (96) are placed adjacent each other at one end (an accessible end) of stay-cable (94) for bridge (88). Typically, these stay-cables (94) extend between a top end of bridge tower (92) and bridge deck (90) upon which traffic is carried. In this manner, an evaluation of the entire length of stay-cable (94) can be achieved with access only to one end of the cable. No particular physical acoustic coupling is required and the transducers could typically be those of the type disclosed in FIG. 4.

An evaluation of an entire bridge structure might involve the progressive analysis of each of the individual stay-cables (94) by moving receiving and transmitting coils (98 and 96) progressively from one stay-cable (94) to the next, each time acquiring a signature and each time performing either an immediate analysis or simply recording that signature data for later comparison with subsequent evaluations.

Figure 7:
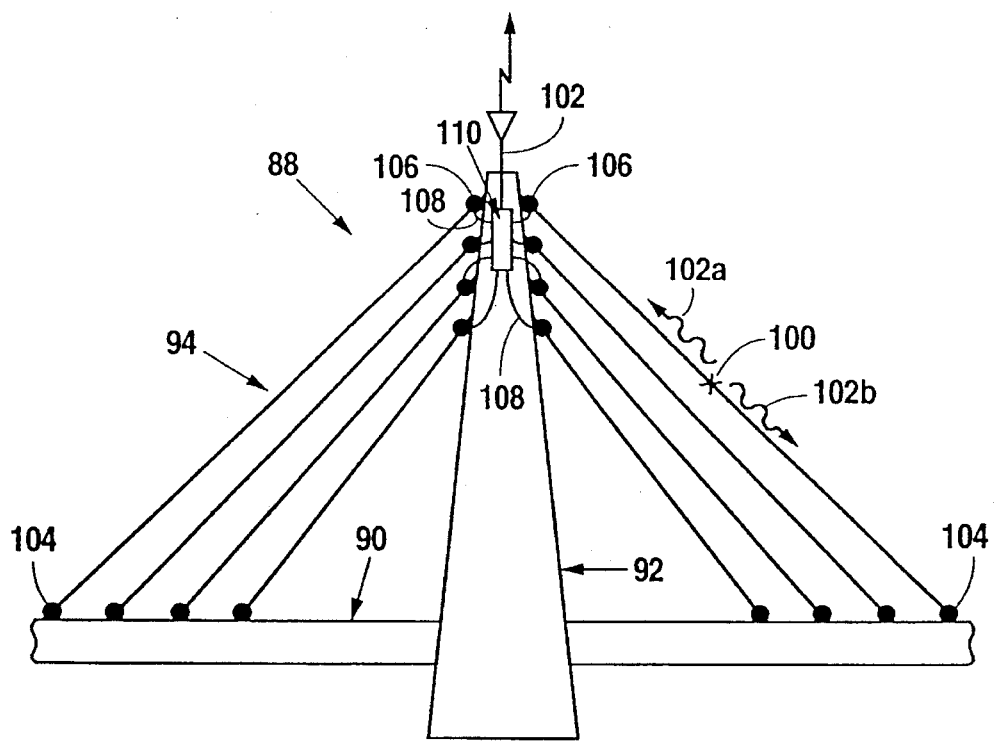
FIG. 7 is a schematic representation of the implementation of the apparatus of the present invention for the magnetostrictive acoustic emission monitoring of cable-stay bridge cables.

Reference is now made to FIG. 7 for a schematic depiction of the implementation of a passive magnetostrictive AE monitoring installation of the type described by the present invention. In lieu of progressively attaching a receiving and transmitting coil to each of stay-cables (94), individual receiver coils or magnetostrictive AE sensors (104 and 106) are placed at terminal ends of stay-cables (94) as permanent installations. Each of these sensors (104 and 106) is then connected to appropriate electronics (110) for amplifying and either recording the existence of an acoustic emission or producing an alarm in response thereto. As shown in the diagram of FIG. 7, a fracture (100) that occurs at a particular location in stay-cable (94) generates acoustic emissions (102a and 102b) which travel in both directions along stay-cable (94). These acoustic emissions (102a and 102b) are thereafter detected by sensors (104 and 106) located at each end of stay-cable (94). An analysis of the time characteristics involved in the reception of each of these acoustic emissions (102a and 102b) and an analysis of the frequencies and amplitudes associated with the signal allow the identification of the location of fracture (100) along stay-cable (94) and, to some extent, its degree of deterioration. Continuous or periodic monitoring according to this method can be implemented.

Figure 8:
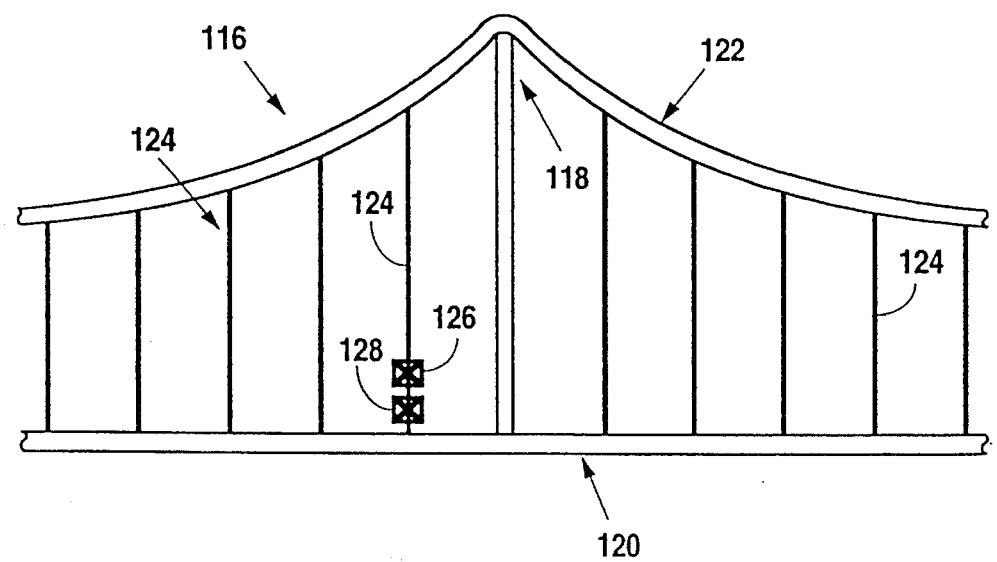
FIG. 8 is a schematic representation of the implementation of the apparatus of the present invention for magnetostrictive acoustic/ultrasonic inspection of suspender ropes of a classic suspension bridge.

Reference is now made to FIG. 8 for an alternative installation of the magnetostrictive acoustic/ultrasonic method of inspecting cables on a second typical bridge structure. In this case, main cables (122) on bridge (116) are used to support suspender ropes (124) that themselves extend between main cable (122) and deck (120) of bridge (116). As with the application described in FIG. 6, a progressive testing of each of the individual suspender ropes (124) can be made, each time obtaining a signature for the rope that can be immediately analyzed or compared with later signatures acquired over time. Here also, access is only required at one end of suspender ropes (124) so that the entire length of cable can be tested.

Figure 9A:
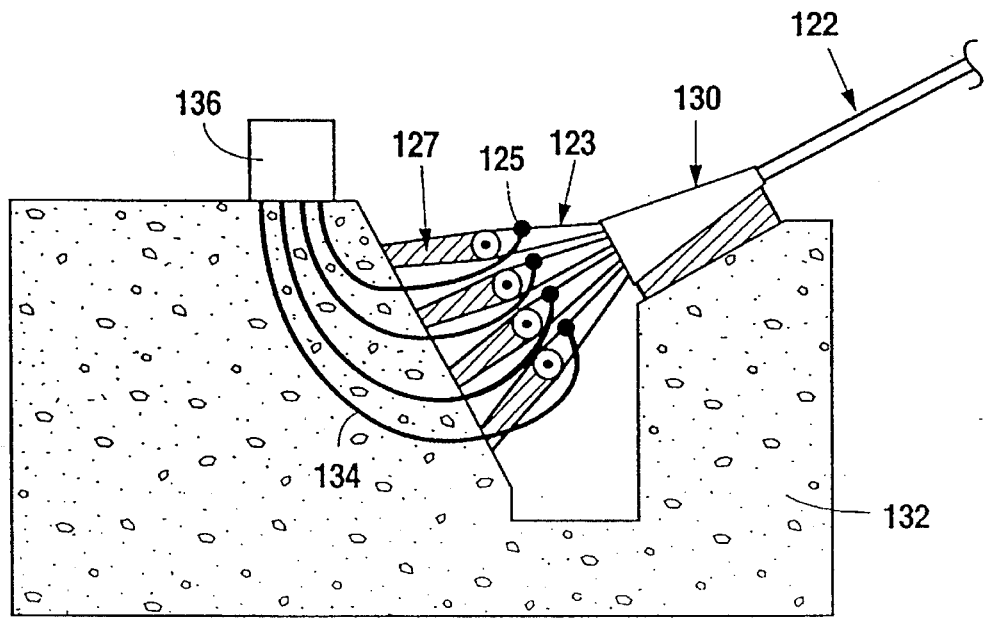
FIG. 9a is a detailed view of the implementation of magnetostrictive AE sensors at the terminal end of a main cable of a classic suspension bridge.
Figure 9B:
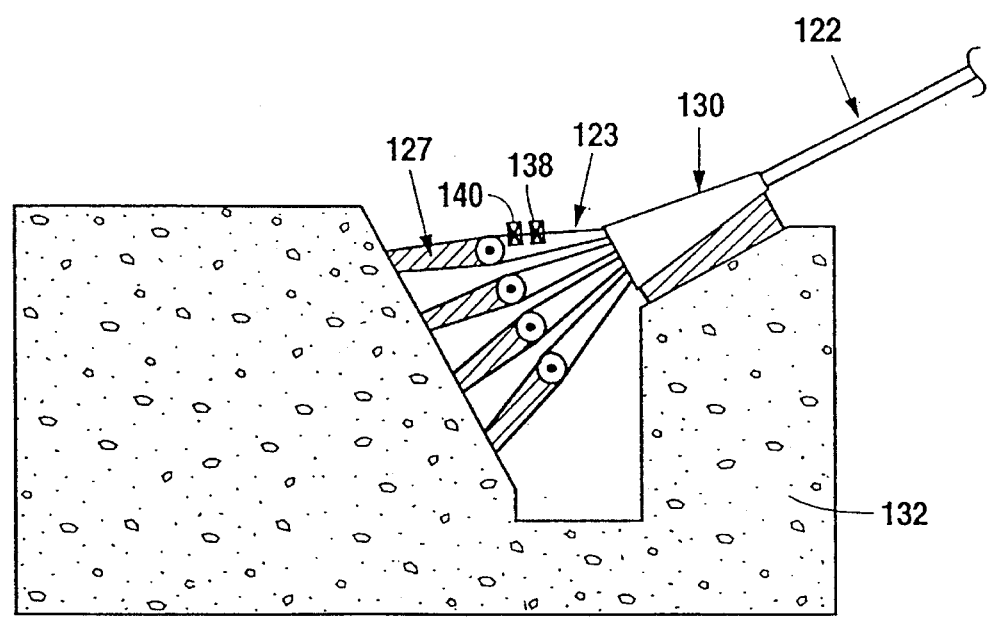
FIG. 9b is a detailed view of the implementation of magnetostrictive acoustic/ultrasonic inspection sensors at the terminal end of a main cable of a classic suspension bridge such as that in FIG. 9.

Reference is now made to FIGS. 9a and 9b for a detailed description of the installation of the present invention on the main cables of a typical suspension bridge structure. FIG. 9a shows the application of the present invention in the magnetostrictive AE monitoring embodiment and FIG. 9b the magnetostrictive acoustic/ultrasonic embodiment. In either case, sensors need only be placed at a terminal end of the main cable of a suspension bridge in order to appropriately detect fractures and anomalies in the main cable. FIG. 9a discloses in detail one terminal end of main cable (122) showing the positioning of magnetostrictive AE sensors (125) which might be installed with the construction of the bridge itself. These permanently installed sensors (125) would be attached to each of individual strands (123) associated with main cable (122) and thereby more accurately determine the specific source of acoustic emissions and thus the fractures that are occurring. In this case, sensors (125) could be connected either to the appropriate electronics (136) as shown, that records the signals received or to an electronically controlled alarm (not shown) that alerts an observer to a condition within main cable (122) that requires attention.

It is anticipated that it would be appropriate to utilize both embodiments of the present invention in combination by applying a magnetostrictively induced acoustic/ultrasonic signal to a cable or other structure once the passive system has detected an acoustic emission worth noting. In other words, AE sensors (125 in FIG. 9a) could be placed permanently at the terminal ends of a structure and would alert a test operator to the necessity of a more thorough analysis of the integrity of the structure by the introduction of a magnetostrictive acoustic/ultrasonic apparatus as described.

FIG. 9b is similar to FIG. 9a and describes the placement of transmitting coil (140) and receiving coil (138) on the same terminal end of main cable (122) of a suspension bridge. Because of the ability to specifically locate the combination of transmitting coil (140) and receiving coil (138) in the active magnetostrictive acoustic/ultrasonic inspection system of the present invention, the most efficient and accurate locations for isolating the fracture or other anomaly can be chosen. It is envisioned that AE sensors would be accurate enough to initially identify the general location of the fracture or other anomaly and that subsequent measurements made with specifically positioned magnetostrictive acoustic/ultrasonic equipment could more accurately locate the fracture or anomaly and identify the degree of deterioration that it reflects.

Figure 10:
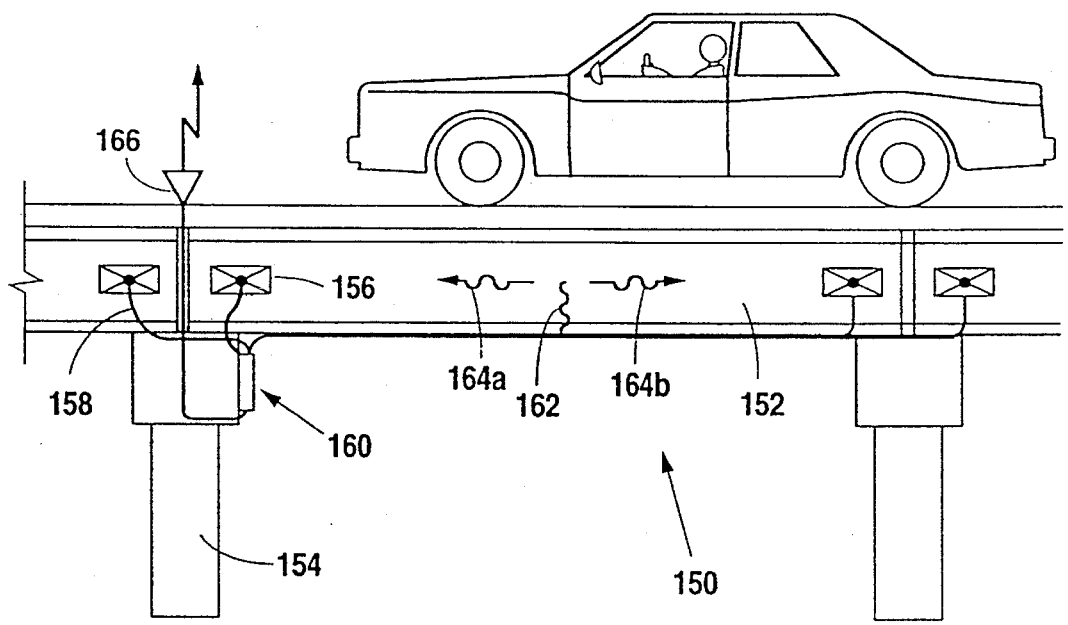
FIG. 10 is a schematic representation of the implementation of the apparatus of the present invention for the magnetostrictive AE monitoring of a steel girder highway bridge.

Reference is now made to FIG. 10 for a detailed description of a similar AE application of the present invention wherein ordinary bridge girder structures might be analyzed and/or monitored. As indicated above, the magnetostrictive effect relies upon the dilational/constrictional motion of a ferromagnetic material in response to an acoustic/ultrasonic wave, in order to achieve the accuracy of detection. However, it is not necessary that the entire structure through which the acoustic wave travels be made of ferromagnetic material, only that area of the structure that is in proximate position to the coils of the sensors, such that the acoustic vibration therein creates the varying magnetic field measurable by the sensors. The representation shown in FIG. 10, therefore, could involve a bridge of a composite structure including both ferromagnetic and non-ferromagnetic materials. Non-ferromagnetic material structures are described in more detail with respect to FIG. 4 11 below.

In FIG. 10, a magnetostrictive AE monitoring system is set up such that over a long term period of time, fractures (162) and other anomalies within steel girders (152) on bridge (150) can be detected as they progressively deteriorate. As shown in FIG. 10, receiving coils (156) might be located at each terminal end of each steel girder (152) in bridge (150). These receiving coils (156) would translate any acoustic emissions (164a and 164b) carried within girder (152) into a signal indicative of a fluctuating magnetic field that results from the magnetostrictive effect caused by the acoustic/ultrasonic wave. This signal generated by receiving coil (156) is then carried to the appropriate electronics (160) that would either record the signal information and associate it with a particular time, or trigger alarm (166) that might easily be monitored by the appropriate personnel.

It is envisioned that alarm (166) associated with such structures could take the form of a radio transmitter alerting a central office of problems with a particular bridge structure or a simple flashing light that would alert a periodic inspector of problems. In the alternative, electronics (160) of the system could simply record the signals in digital or magnetic medium in a manner that could be periodically retrieved and analyzed for problems. As long as the time factor is tracked and the physical dimensions of the bridge structure and the placement of the sensors are known, an accurate determination of the location of fracture (162), and to a great extent its degree of deterioration, can be obtained. The electronics for such a structure could be centralized in a single unit (as with 160) with each sensor being individually identified by centralized unit (160) in a manner well known in the field.

Figure 11:
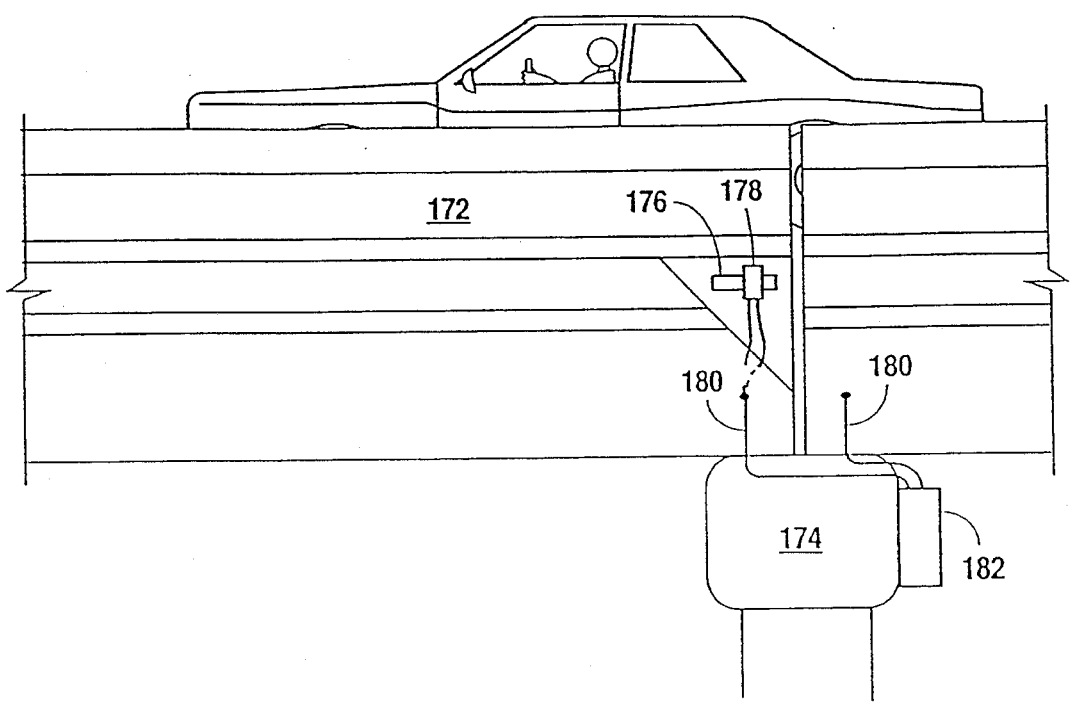
FIG. 11 is a schematic representation of the implementation of the apparatus of the present invention for the magnetostrictive AE monitoring of a bridge comprised of prestressed concrete with ferromagnetic reinforcing rods, prestressing strands and post-tensioning rods or tendons.

Reference is now made to FIG. 11 for an application of the present invention in a structure that is not comprised primarily of ferromagnetic material. Most modern simple highway bridge structures are comprised not of steel girders, but of prestressed concrete beams that incorporate reinforcing steel rods and prestressed tendons within them. In FIG. 11, a typical bridge structure is shown with the magnetostrictive AE monitoring system in place. Very similar to the installation shown in FIG. 10 the distinctive feature of the application in FIG. 11 is the attachment of AE sensors (178) directly to prestressing strands and post-tensioning rods, as well as reinforcing rods (176) within concrete beams (172). As the detail shows, imbedded within concrete beam (172) is coil sensor (178) surrounding one end of an internal reinforcing rod (176). Because up to the point of sensor (178), it is only necessary that acoustic/ultrasonic waves travel through the structure under evaluation, as long as the concrete (non-ferromagnetic material) is acoustically coupled to reinforcing rod (176), magnetostrictive AE sensor (178) will detect fractures and other anomalies within concrete beam (172) that may or may not be directly associated with reinforcing rod (176). In other words, a crack that might form in the concrete over a period of time would emit acoustic waves that would travel to reinforcing rod (176) and thereby travel to the location of sensor (178). The acoustic waves within reinforcing rod (176) would generate or cause the magnetostrictive effect in a manner that is detectable by coil sensor (178). Sensor (178) could thereafter function in much the same way as in its monitoring of materials made entirely of ferromagnetic substances. Here again, a central or periodic electronic recording or alarm device (182) would be installed that would alert the appropriate personnel as necessary.

It is envisioned that such sensors could be installed when the concrete beams are manufactured and could thereafter be attached to the monitoring system upon installation of the bridge structure. It is also possible, however, that such sensors could be placed within or on existing structures with little retrofit problem. Again, the only important coupling is an acoustic coupling between the structure under evaluation and a section of material made of ferromagnetic substance. It would be possible, for example, to take a structure made entirely of concrete, or a structure whose internal steel reinforcing rods are inaccessible, and acoustically couple a ferromagnetic plate to the exterior surface. This ferromagnetic plate would act as an acoustic "microphone" that would generate a fluctuating magnetic field in response to the passage of acoustic waves therethrough. The sensors described by the present application could, therefore, pick up such magnetostrictive effects that result from the passage of acoustic waves through the ferromagnetic material and translate these effects into signals capable of analysis and interpretation for the existence of fractures and other detrimental anomalies.

Carrying the example of FIG. 11 to its logical extension, it is anticipated that generally non-ferromagnetic material structures could be created with a fine internal network of ferromagnetic wires, non-ferromagnetic metallic wires, or non-metallic fibers coated with ferromagnetic materials that, although lending little if any structural integrity to the substance, provide a means whereby the magnetostrictive effect could be measured throughout the entire substance. A road surface, for example, could be underlayered with a very fine, lightweight ferromagnetic net or webbing that could be interspersed with minute receiving coils at periodic intervals. These receiving coils would sense acoustic emissions within the road surface structure and translate these emissions into signals that could be easily analyzed for the occurrence of growing fractures, stresses, and other anomalies. Obviously, a number of external factors would remain that required identification and compensation for, but if a typical "signature" for a particular area of the material under evaluation could be obtained, then periodic comparisons would be able to isolate changes and growing anomalies.

ALTERNATE PREFERRED EMBODIMENT OF THE PRESENT INVENTION

Nondestructive evaluation of non-ferromagnetic materials especially for the purpose of monitoring dynamic strains, crack and delamination growth, and impact damage is particularly appropriate for the acoustic emission mode of the present invention. While the present invention is primarily suited to ferromagnetic materials and especially such materials that are longitudinal in structure such as cables and ropes, it is just as readily appropriate for similar evaluations of non-ferromagnetic or non-magnetic structures, as long as such structures have been previously imbedded with ferromagnetic or magnetic materials.

Figure 12:
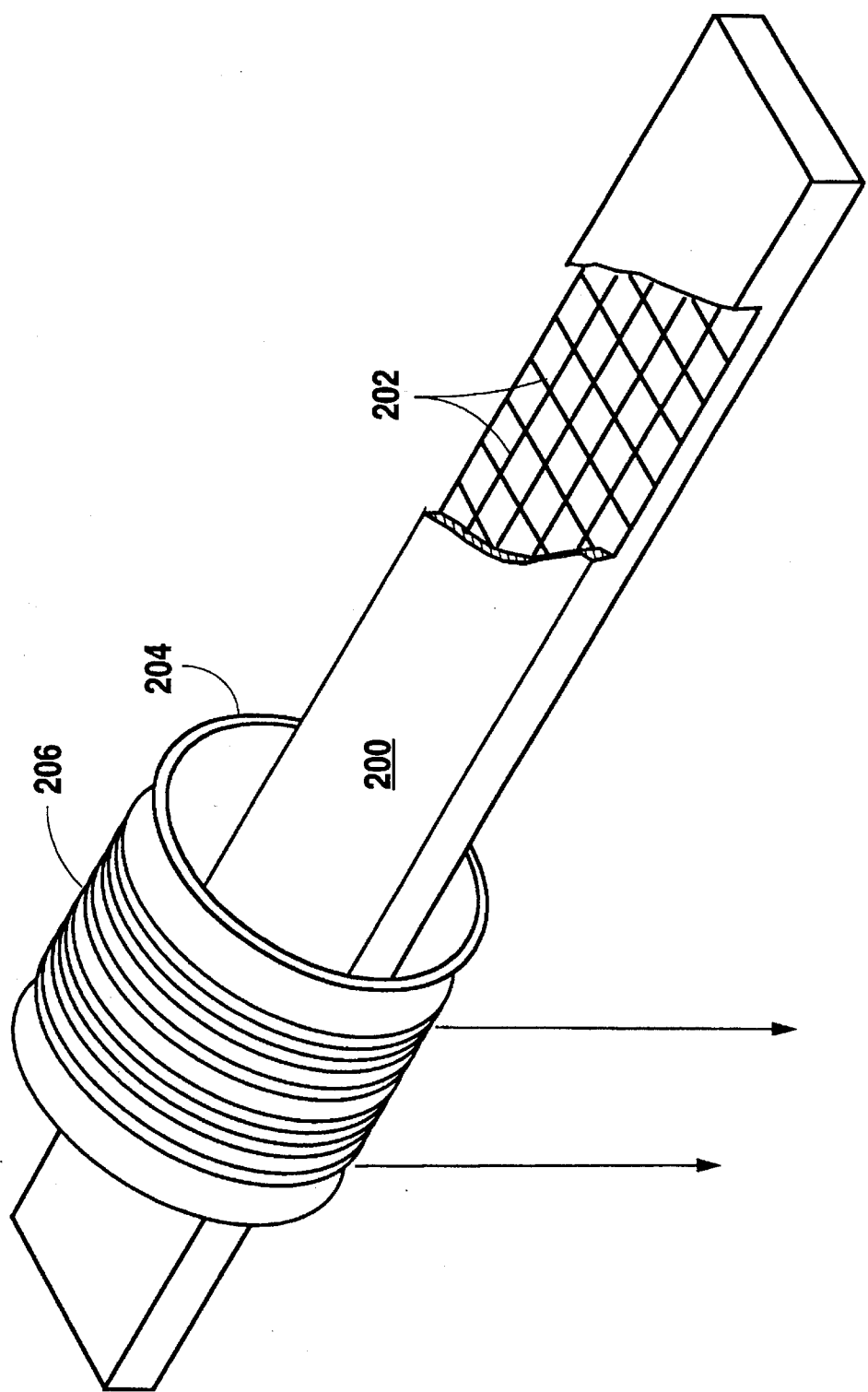
FIG. 12 is a perspective view of the structural configuration of an alternative preferred embodiment of the present invention.

As an example, a graphite/epoxy composite specimen can be easily constructed according to well known techniques with small diameter (0.004") nickel wires imbedded within or below the first ply of the specimen. FIG. 12 shows the basic structural configuration for this example of an alternative embodiment of the present invention. In FIG. 12, composite specimen (200) incorporates small diameter nickel wires (202) below its first ply as shown, and additionally incorporates encircling pickup coil (204) as a sensor for the magnetostrictive effect. Since nickel is a magnetic material, any vibrations, movements, or other acoustic emissions that occur within composite specimen (200) will, through acoustic coupling, be transferred to nickel wires (202). Vibration resulting from the acoustic waves within composite specimen (200) and within nickel wires (202) will generate a magnetic flux that results from the vibration of the magnetic material found in nickel wires (202). This magnetic flux is, as described in the previous embodiment, detectable by encircling pickup coil windings (206).

Figure 13:
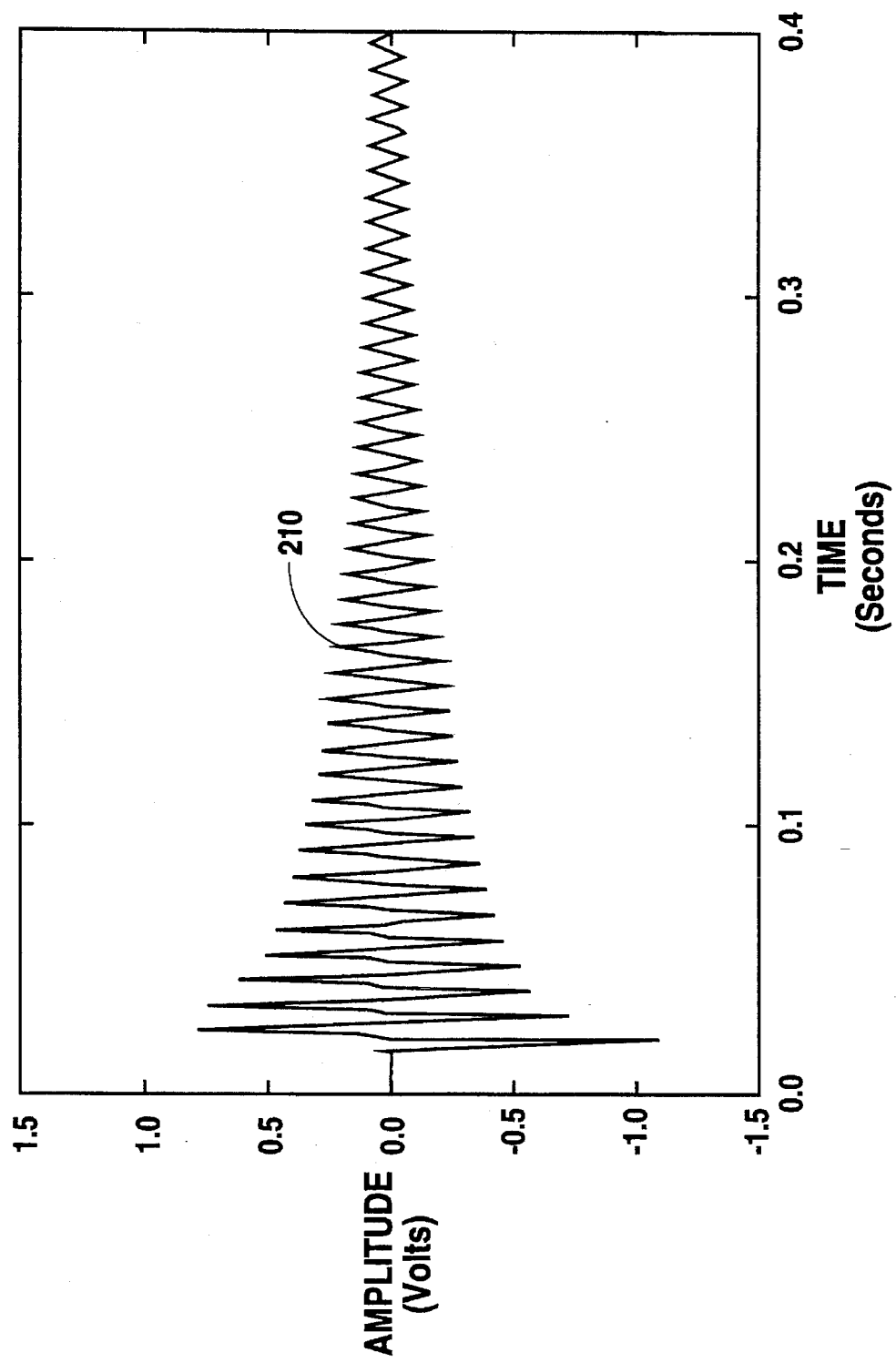
FIG. 13 is a graphic representation of the response of a vibrating specimen shown in FIG. 12.

Tests were run with the composite specimen shown in FIG. 12 mounted in a cantilever configuration to record the natural damped vibration (dynamic strain) of the specimen. FIG. 13 is a graphic representation of the response of the vibrating specimen after it was set in motion by a simple deflection of the free end. Signal (210) indicated in FIG. 13 was received by the encircling pickup coil shown in FIG. 12 which is itself responsive to fluxuations in the magnetic field surrounding the specimen that are attributable to the magnetostrictive effect created by the nickel wires within the specimen.

Figure 14:
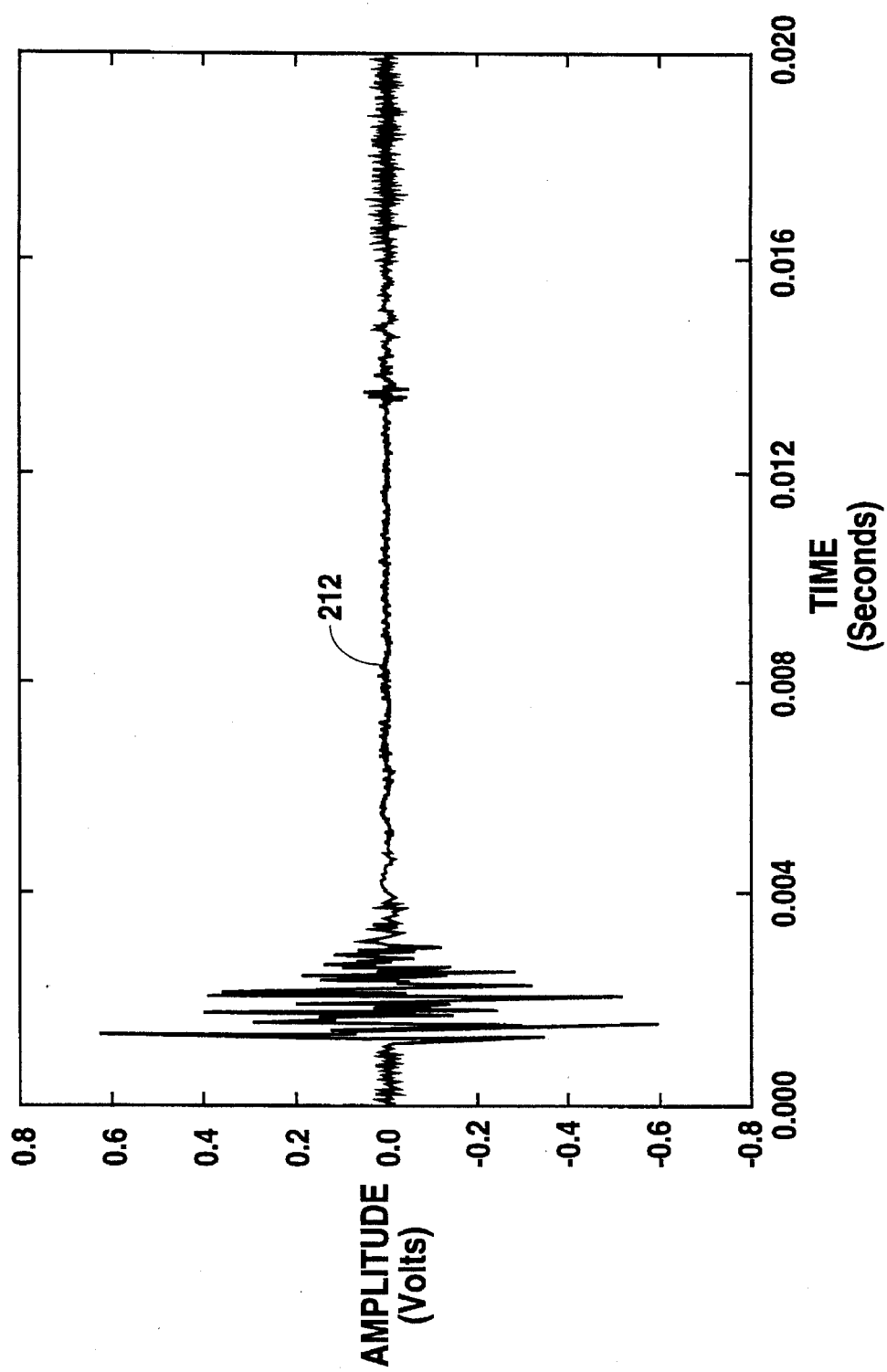
FIG. 14 is a graphic representation of the signal resulting from a standard acoustic emission input signal, simulating crack growth for the specimen shown in FIG. 12.

In addition, the specimen was subjected to a 0.5 mm pencil lead break which is the standard acoustic emission input signal that simulates crack growth in a medium under evaluation. FIG. 14 is a graphic representation of the signal (212) results that from this test. The signal characteristics in FIG. 14, especially the high frequency content of the signal, allows for the characteristic identification of such crack growth acoustic emissions as opposed to the dynamic strain emissions shown in FIG. 13.

Figure 15:
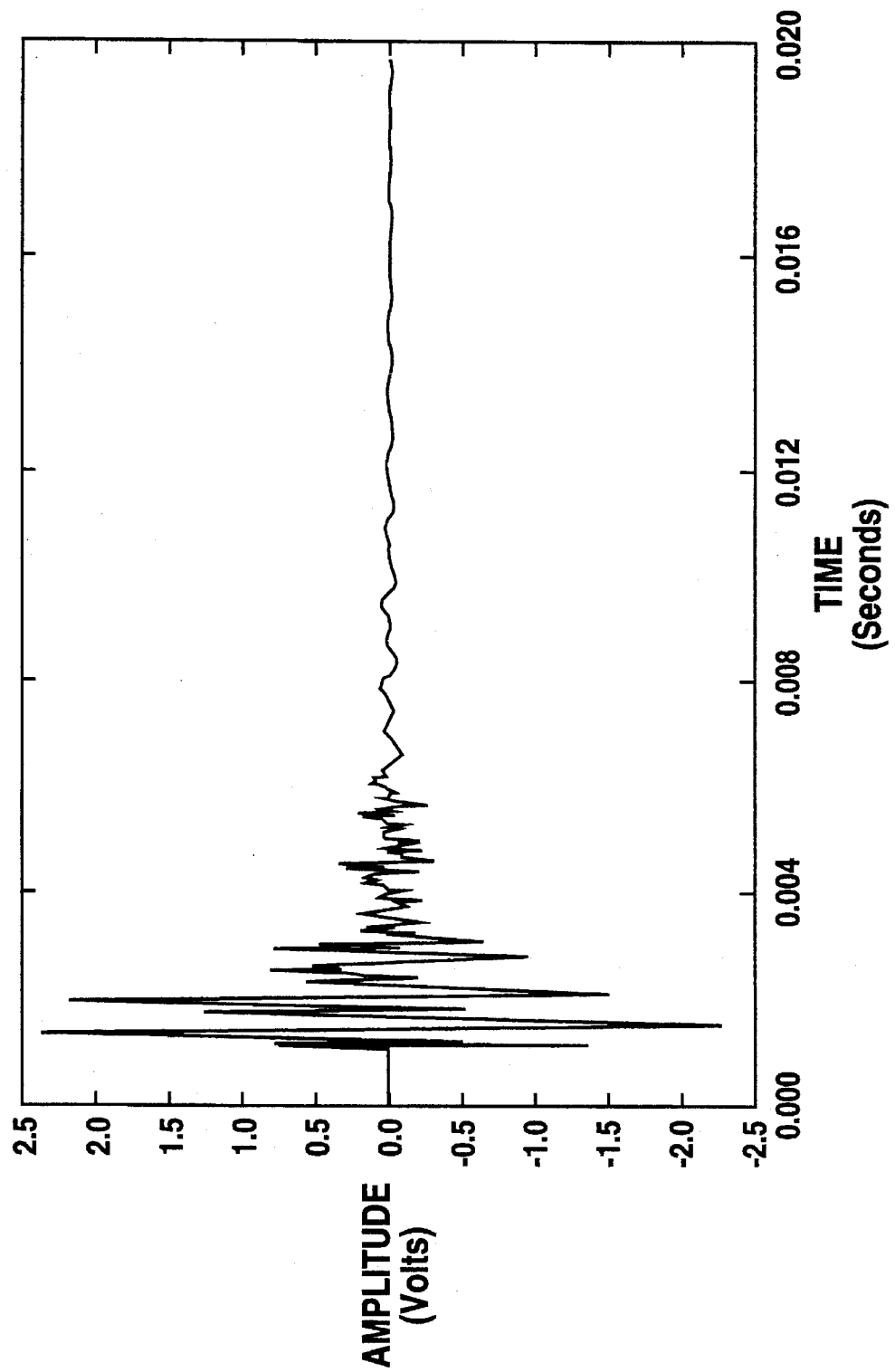
FIG. 15 is a graphic representation of a signal resulting from an impact response for the specimen shown in FIG. 12.

Finally, to further identify typical signals that might be expected in the passive evaluation of a medium under study, a 0.375" diameter steel ball was dropped from a height of about 4.5" to create an impact response in the material. FIG. 15 is a graphic representation of signal (214) received by the encircling pickup coil as a result of this test. It can be seen from FIG. 15 that the frequency response is intermediate between the damped vibration (dynamic strain) response and the simulated crack growth response. It is, therefore, possible to characteristically identify a number of different events and developments in the internal structure of a composite specimen. Each of these events and conditions have distinctive signal features and excellent signal to noise ratios when the magnetostrictive sensors is utilized in the above described manner.

Taking the initial damped vibration test described above, and the associated signal depicted in FIG. 13 to other applications, it can be seen that the technology of the present invention can accurately characterize changes in the dynamic strain that a material is being subjected to. By comparing a "signature" signal with subsequently detected signals for the same material, a measure of dynamic strain can be made based upon a history for that same material or materials of a similar composition and configuration.

While a number of applications of each of the preferred embodiments of the present invention have been identified, it is anticipated that one skilled in the art would identify further applications of each of these methods and each apparatus described, in a manner consistent with the procedures associated with the present invention. It is anticipated that the present invention would have applications in any environment where remote nondestructive evaluation of materials is required and a ferromagnetic substance is present, or may be introduced with little or no adverse effect.

We claim:

1. A method for the non-destructive monitoring of a non-ferromagnetic material for the growth of fractures, cracks, dynamic strains, and delamination, as well as impact damage and other anomalies comprising the steps of:

dispersing a magnetic material throughout a volume of said non-ferromagnetic material subject to said non-destructive monitoring;

detecting changes in a magnetic field about said magnetic material as a result of a passage of acoustic waves within said magnetic material and said non-ferromagnetic material, said changes in said magnetic field caused by an inverse magnetostrictive effect resulting from said passage of said acoustic waves, said acoustic waves being generated by said fractures, cracks, dynamic strains, delaminations, and other anomalies in said non-ferromagnetic material;

analyzing said detected changes in said magnetic field indicative of said acoustic waves, and correlating said detected changes with patterns of changes known to be indicative of said growth of said fractures, cracks, dynamic strains, delaminations, and other anomalies in said non-ferromagnetic material.

2. The method of claim 1 further comprising the step of:

establishing a DC bias magnetic field in a localized area of said non-ferromagnetic material prior to detecting changes in said magnetic field.

3. The method of claim 1, wherein said step of detecting changes in said magnetic field comprises placing an electromagnetic coil proximate to said localized area of said non-ferromagnetic material containing said magnetic material, and detecting variations in a voltage induced in said electromagnetic coil.

4. An apparatus for the non-destructive monitoring of non-ferromagnetic material comprising a disperse in network of magnetic material within said non-ferromagnetic material;

receiving coil positioned adjacent to or encompassing a localized area of said non-ferromagnetic material proximate to said network of magnetic material;

bias magnet adjacent said receiving coil, said bias magnet creating a DC magnetic field within and around said localized area of said non-ferromagnetic material;

signal conditioner for amplifying and filtering a voltage from said receiving coil, said amplified and filtered voltage being a signal indicative of fluxuations in said magnetic field; and recording means for storing said signal and for subsequently allowing a test operator to interpret said signal and thereby interpret said fluxuations in said DC magnetic field;

wherein said fluxuations in said DC magnetic field results from a magnetostrictive effect caused by acoustic waves within said non-ferromagnetic material, said acoustic waves being generated from said fractures, cracks, and other anomalies within said non-ferromagnetic material.

5. The method of claim 1, wherein said magnetic material comprises a network of wires dispersed through said non-ferromagnetic material with a density and with a structure sufficient to provide resolution of said growth of said fractures, cracks, delaminations, dynamic strains, and other anomalies.

* * * * *